United States Patent
Downham et al.

(12)

(10) Patent No.: US 6,916,808 B2
(45) Date of Patent: Jul. 12, 2005

(54) 2-THIO-4H-3, 1-BENZOXAZIN-4-ONE DERIVATIVES FOR USE AS ENZYME INHIBITORS

(75) Inventors: Robert Downham, Cambridge (GB); Richard Michael John Palmer, Hayes (GB); Harold Francis Hodson, Beckenham (GB); Christopher Robert Dunk, Ely (GB)

(73) Assignee: Alizyme Therapeutics Limited, Cambridge (GB)

( * ) Notice: Subject to any disclaimer, the term of this patent is extended or adjusted under 35 U.S.C. 154(b) by 55 days.

(21) Appl. No.: 10/181,868
(22) PCT Filed: Jan. 17, 2001
(86) PCT No.: PCT/GB01/00171
§ 371 (c)(1), (2), (4) Date: Nov. 27, 2002
(87) PCT Pub. No.: WO01/53278
PCT Pub. Date: Jul. 26, 2001

(65) Prior Publication Data
US 2003/0176429 A1 Sep. 18, 2003

(30) Foreign Application Priority Data
Jan. 24, 2000 (GB) .............................................. 0001572

(51) Int. Cl.[7] .................... C07D 498/04; C07D 405/12; C07D 403/14; A61K 31/536; A61K 31/5365
(52) U.S. Cl. .......................... 514/230.5; 544/92; 544/91
(58) Field of Search .......................... 544/92; 514/230.5

(56) References Cited

FOREIGN PATENT DOCUMENTS

| WO | WO 00/40247 | 7/2000 |
|---|---|---|
| WO | WO 00/40569 | 7/2000 |

OTHER PUBLICATIONS

NIDDK Weight—control Information Network at <http://www.niddk.nih.gov/health/nutri/pubs/health.htm>, downloaded on Jun. 3, 2004 (9 pages).*
Chalmers (TIPS vol. 17, pp. 166–172 Apr. 1996).*
Thomas A. Godwin (Gastrointestinal Diseases, <http://edcenter.med.cornell.edu/CUMC_PathNotes/Gastrointestinal/Gastrointestinal.html>downloaded on Jun. 4, 2004, (51 pages).*
Krantz et al., "Design and synthesis of 4H-3, 1–benzoxazin–4–ones as potent alternate inhibitors of human leukocyte elastase", *J. Med. Chem.* 33:464–479, 1990.
Robinson et al., "13–C nuclear magnetic resonance and reactivity of 4H-3, 1–benzoxazin–4–ones", *Can. J. Chem.* 66:416–419, 1988.
Copy of International Search Report for PCT/GB01/00171.

* cited by examiner

*Primary Examiner*—Mark L. Berch
*Assistant Examiner*—Kahsay Habte
(74) *Attorney, Agent, or Firm*—Brenda Herschbach Jarrell; Charles E. Lyon; Choate, Hall & Stewart LLP

(57) ABSTRACT

The use of a compound, comprising formula (I) or a salt, ester, amide of prodrug thereof in the inhibition of an enzyme whose preferred mode of action is to catalyse the hydrolysis of an ester functionality e.g. in the control and inhibition of unwanted enzymes in products and processes. The compounds are also useful in medicine e.g. in the treatment of obesity and related conditions. The invention also relates to novel compounds within formula (I), to processes for preparing them and pharmaceutical compositions containing them. In formula (I) A is an optionally substituted 6-membered aromatic or heteroaromatic ring; and $R^1$ is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups (I)

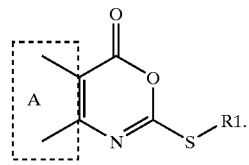

30 Claims, No Drawings

2-THIO-4H-3, 1-BENZOXAZIN-4-ONE DERIVATIVES FOR USE AS ENZYME INHIBITORS

The present invention provides benzoxazinone compounds, their use in the inhibition of an enzyme whose preferred mode of action is to catalyse the hydrolysis of an ester functionality, their use in medicine, and particularly in the prevention and/or treatment of obesity or an obesity-related disorder. Also provided are methods for the prevention and/or treatment of obesity or an obesity-related disorder and for promoting/aiding non-medical weight loss and the use of the compounds in the manufacture of a medicament for the aforementioned indications. The invention also provides processes for manufacture of said compounds, compositions containing them and methods for manufacturing such compositions.

In the last 20 years, there has been an increasing trend in obesity in the populations of the developed world. The increased incidence of obesity is due in part to the ready availability of food in numerous retail outlets and westernised diets that have high saturated fat and lower fibre contents such that the food is energy dense. The lifestyle of the populations of the developed world has also become more sedentary with the increased mechanisation of society and the steady reduction of manual labour intensive industries. There now exists an energy imbalance between the energy intake from calorie dense foods and the reduced energy expenditure required for a sedentary lifestyle. Some of the excess energy intake is stored as fat in the adipose tissue, the accumulation of which over a period of time results in obesity and can be a significant contributory factor to other disease and disorders.

Obesity is now recognised by the medical profession as a metabolic disease. In the USA, it is estimated that 25% of the adult population is considered clinically obese (Body Mass Index>30). Obesity can be a debilitating condition which reduces the quality of life and increases the risk of related disorders such as diabetes, cardiovascular disease and hypertension. It has been estimated that $45 billion of US healthcare costs, or 8% per annum of total healthcare spend, is as a direct result of obesity. The traditional approaches to long term weight management such as diet and exercise have proved ineffective alone to control the spread of obesity. Today, more than ever, there is considerable interest in developing safe, effective drugs for the treatment of obesity.

Pharmacological approaches to the treatment of obesity have focused on either developing drugs that increase energy expenditure or drugs that reduce energy intake. One approach to the reduction of energy intake is to reduce the body's ability to digest and absorb food, in particular fat. The key enzymes involved in the digestion of fat are hydrolytic enzymes. The most significant of the fat degrading enzymes are lipases, primarily, but not exclusively pancreatic lipase that is secreted by the pancreas into the gut lumen. The lipase inhibitor lipstatin has formed the basis of the anti-obesity drug, orlistat. European Patent Application No. EP129748, relates to Orlistat and related compounds and their use in inhibiting pancreatic lipase and treating hyperlipaemia and obesity.

Even if orlistat provides an effective method for treating obesity, there remains a need to provide alternative drugs and methods for use in the control and treatment of obesity and obesity-related disorders and in promoting or aiding non-medical weight loss. Inhibitors of enzymes involved in the degradation of fat are provided here and shown to be effective in the prevention and/or treatment of obesity, obesity-related disease and/or in promoting cosmetic weight loss.

Krantz et al., *J. Med. Chem.*, 1990, 33(2); 464–469 describes benzoxazinones of formula

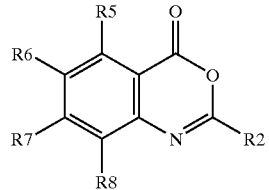

wherein $R^2$ is inter alia MeS—, EtS—, iPrS, BnS—, —SCH$_2$COOEt, —SCH$_2$CH=CHPh, 3-indolyl-CH$_2$S— and 4-imd-CH$_2$S—; $R^5$ is variously hydrogen, methyl or ethyl; $R^6$ is variously hydrogen, methyl, methoxy, HNAC or NMe$_2$; $R^7$ is variously hydrogen, ethyl or methoxy or $R^6$ and $R^7$ together represent a group —CH=CH—CH=CH—; and $R^8$ is variously hydrogen or methyl. The compounds are said to be inhibitors of human leukocyte elastase.

International application numbers PCT/GB00/00032 and PCT/GB00/00031 relate to 2-oxy and 2-amino benzoxazinone compounds. These applications provide alternative methods for use in the control and treatment of obesity and obesity-related disorders.

We have now found that a particular class of benzoxazinone compounds has activity as lipase inhibitors.

Accordingly, in a first aspect, the present invention provides the use of a compound of formula (I):

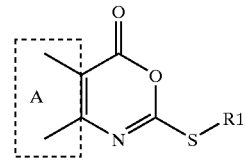

(I)

or a pharmaceutically acceptable salt, ester, amide or pro-drug therof;
in the manufacture of a medicament for the treatment of conditions requiring the inhibition of an enzyme whose preferred mode of action is to catalyse the hydrolysis of an ester functionality;
wherein in formula (I):
A is a 6-membered aromatic or heteroaromatic ring optionally substituted with one or more groups as defined below for $R^1$; and
$R^1$ is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups, wherein the substituents are one or more independently of halogen, alkyl, halo-substituted alkyl, aryl, arylalkyl, heteroaryl, reduced heteroaryl, reduced heteroarylalkyl, arylalkoxy, cyano, nitro, —C(O)R$^4$, —CO$_2$R$^5$, —SOR$^4$, —SO$_2$R$^4$, —NR$^6$R$^7$, —OR$^6$; —SR$^6$, —C(O)CX$^1$X$^2$NR$^6$R$^7$, —C(O)N(OH)R$^6$, —C(O)NR$^5$R$^4$, —NR$^6$C(O)R$^4$, —CR$^6$(NH$_2$)CO$_2$R$^6$, —NHCX$^1$X$^2$CO$_2$R$^6$, —N(OH)C (O)NR$^6$R$^7$, —N(OH)C(O)R$^4$, —NHC(O)NR$^6$R$^7$, —C(O)NHNR$^6$R$^7$, —C(O)N(OR$^5$)R$^6$, or a lipid or steroid (natural or synthetic) with the proviso that any hetero atom substituent in $R^1$ must be separated from the exocyclic sulphur atom by at least two carbon atoms (preferably saturated);

and where:

$R^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, —$OR^6$, —$NHCX^1X^2CO_2R^6$ or —$NR^6R^7$;

$R^5$ is hydrogen, alkyl, alkenyl, alkynyl, cycloalkyl, cycloalkenyl, aryl, arylalkyl heteroaryl, heteroarylalkyl, reduced heteroaryl or reduced heteroarylalkyl; and $R^6$ and $R^7$ are independently hydrogen, alkyl, alkenyl, alkynyl, cycloalkyl, cycloalkenyl, aryl, arylalkyl, heteroaryl, reduced heteroaryl, reduced heteroarylalkyl or —$(CH_2)n(OR^5)m$ wherein n is 1 to 12, preferably 2 to 10, wherein m is 1–3 and $R^5$ is most preferably $C_2$–$C_{10}$ alkyl; and $X^1$ and $X^2$ are independently hydrogen, alkyl, alkenyl, alkynyl, cycloalkyl, cycloalkenyl, aryl, heteroaryl, arylalkyl, heteroarylalkyl, reduced heteroaryl or reduced heteroarylalkyl.

In compounds of formula (I) any alkyl, alkenyl and alkynyl groups and moieties may be straight chain (unbranched) or branched chain. Straight chain alkyl, alkenyl and alkynyl groups or moieties may contain from 1 to 30 carbon atoms, eg. 1 to 25 carbon atoms, preferably 1 to 20 carbon atoms. Branched chain alkyl, alkenyl and alkynyl groups or moieties may contain from 1 to 50 carbon atoms, preferably 1 to 30 carbon atoms. It will be appreciated that alkenyl and alkynyl groups or moieties will contain at least 2 carbon atoms.

Preferred values for $R^1$, $R^4$, $R^5$, $R^6$, $R^7$, $X^1$ and $X^2$ are as defined below for formulae (II).

In this text, 'reduced', in the context of 'reduced heteroaryl' and the like means fully or partially saturated.

Aryl groups include for example optionally substituted unsaturated monocyclic or bicyclic rings of up to 12 carbon atoms, such as phenyl and naphthyl, and partially saturated bicyclic rings such as tetrahydro-naphthyl. Examples of substituents which may be present on an aryl group include one or more of halogen, amino, nitro, alkyl, haloalkyl, alkoxy, phenoxy and phenoxy substituted by one or more of halo, alkyl or alkoxy.

A heteroaryl group or moiety may be for example an optionally substituted 5- or 6-membered heterocyclic aromatic ring which may contain from 1 to 4 heteroatoms selected from O, N and S. The heterocyclic ring may optionally be fused to a phenyl ring. Examples of heteroaryl groups thus include furyl, thienyl, pyrrolyl, oxazolyl, oxazinyl, thiazolyl, imidazolyl, oxadiazolyl, thiadiazolyl, pyridyl, triazolyl, triazinyl, pyridazyl, pyrimidinyl, pyrazolyl, indolyl, indazolyl, benzofuranyl, benzothienyl, benzimidazolyl, benzoxazolyl, benzoxazinyl, quinoxalinyl, quinolinyl, quinazolinyl, cinnolinyl, benzothiazolyl, pyridopyrrolyl. Suitable substituents include one or more of halogen, oxo, amino, nitro, alkyl, haloalkyl, alkoxy, phenoxy and phenoxy substituted by one or more of halo, alkyl, haloalkyl or alkoxy.

A reduced heteroaryl group or moiety may be for example a fully or partially saturated derivative of the aforementioned heteroaryl groups. Examples of reduced heteroaryl groups thus include pyrrolidinyl, tetrahydrofuryl, tetrahydrothienyl and piperidinyl.

The compounds of formula (I) are used in the manufacture of a medicament for the treatment of conditions requiring the inhibition of an enzyme whose preferred mode of action in vivo is to catalyse the hydrolysis of an ester functionality. Such enzymes include lipases, esterases and phosphoesterases.

The compounds of formula (I) are useful inhibitors of enzymes involved in the degradation of fats. Preferably therefore the first aspect of the invention provides the use of a compound of formula (I) as defined hereinabove, or a pharmaceutically acceptable salt, ester, amide or prodrug thereof, in the manufacture of a medicament for the control or treatment of obesity, or obesity-related disorders or for promoting non-medical weight loss.

Preferably, a compound for use according to the first aspect of the invention is a compound of formula (II):

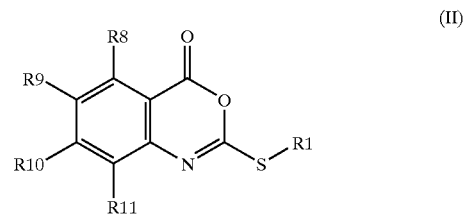

(II)

or a pharmaceutically acceptable salt, ester, amide or prodrug therof, wherein:

$R^1$, $R^4$, $R^5$, $R^6$, $R^7$, $X^1$ and $X^2$ are as defined above for formula (I); and $R^8$, $R^9$, $R^{10}$, $R^{11}$ are each independently hydrogen, halo, hydroxy, amino, nitro, cyano, or a group $R^1$, as defined above, or a group $R^{12}Q$ where Q is O, CO, CONH, NHCO, S, SO, $SO_2$, or $SO_2NH^2$ and $R^{12}$ is hydrogen or a group $R^1$ as defined above, or a group $R^1R^2N$ where $R^1$ is as defined above and $R^2$ is hydrogen or $R^1$, with the proviso that any hetero atom substituent in $R^1$ and/or $R^2$ must be separated from the nitrogen atom substituent by at least two carbon atoms (preferably saturated).

More preferably, a compound for use according to the first aspect of the invention comprises a compound of formula (II), or a pharmaceutically acceptable salt, ester, amide or prodrug therof; wherein:

$R^1$ is either a branched or unbranched alkyl group having up to 25, e.g. up to 20 carbon atoms, an aryl (e.g. optionally substituted phenyl or 2-naphthyl), an arylalkyl group wherein the alkyl moiety has up to 25, e.g. up to 20 carbon atoms, or an arylaryl group, wherein the arylalkyl group or the arylaryl group may be separated by a spacer, and where the spacer can be one or more of an ester, amide, O, $CH_2$ or a ketone and wherein any aryl group is preferably a phenyl, optionally substituted with alkyl, haloalkyl or halogen;

$R^8$ is hydrogen or fluorine;

$R^9$ is lower branched or unbranched alkyl having 1 to 10 carbon atoms, preferably methyl; cyclic alkyl having 3 to 10 carbon atoms, preferably cyclopropyl; haloalkyl, preferably trifluoromethyl; or a halogen, most preferably chlorine or fluorine;

$R^{10}$ is hydrogen; lower branched or unbranched alkyl having 1 to 10 carbon atoms, preferably methyl; cyclic alkyl having 3 to 10 carbon atoms, preferably cyclopropyl; haloalkyl, preferably trifluoromethyl; or a halogen, most preferably chlorine or fluorine;

$R^{11}$ is hydrogen; lower branched or unbranched alkyl having 1 to 10 carbon atoms, preferably methyl; or halogen, preferably fluorine.

In particular, $R^1$ is an unbranched alkyl group, having 12, 14, 15, 16, 17 or 18 carbon atoms in the alkyl chain. In addition to this particular option for $R^1$, $R^9$ may be methyl.

In a second aspect, the present invention provides novel compounds of formulae (I) or (II) as defined hereinabove, and pharmaceutically acceptable salts, esters, amides and prodrugs thereof, with the proviso that the following compounds are excluded:

| $R^1$ | $R^8$ | $R^9$ | $R^{10}$ | $R^{11}$ |
|---|---|---|---|---|
| Me | H | H | H | H |
| Me | Me | H | H | H |
| Et | H | H | H | H |
| Et | Me | H | H | H |
| Et | Et | H | H | H |
| Et | H | Me | H | H |
| Et | H | HNAC | H | H |
| Et | H | OMe | OMe | H |
| Et | H | NMe₂ | H | H |
| Et | H | H | Et | H |
| Et | H | H | H | Me |
| Et | H | —CH=CH—CH=CH— | | H |
| iPr | H | H | H | H |
| Bn | H | H | H | H |
| Bn | H | H | H | Me |
| Bn | H | OMe | OMe | H |
| Bn | H | —CH=CH—CH=CH— | | H |
| CH₂COOEt | H | H | H | H |
| CH₂CH=CHPh | H | OMe | OMe | H |
| 3-indolylCH₂ | H | OMe | OMe | H |
| 4-imdCH₂ | H | OMe | OMe | H |

In a preferred feature of the second aspect, the present invention provides novel compounds of formula (Ia):

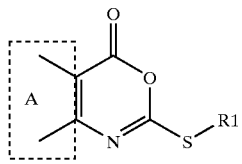

(Ia)

or a pharmaceutically acceptable salt, ester, amide or prodrug therof;
wherein in formula (Ia):
A is an optionally substituted 6-membered aromatic or heteroaromatic ring; and
$R^1$ is a branched $C_{4-50}$alkyl or unbranched $C_{3-25}$alkyl (with the alkyl group optionally interrupted by one or more oxygen atoms), $C_{2-25}$alkenyl, $C_{2-25}$alkynyl, $C_{3-10}$cycloalkyl, $C_{3-10}$cycloalkenyl, aryl, aryl$C_{2-25}$alkyl, reduced aryl$C_{1-25}$alkyl, aryl$C_{2-25}$alkenyl, heteroaryl, heteroaryl$C_{2-25}$alkyl, heteroaryl$C_{2-25}$alkenyl, reduced aryl, reduced heteroaryl, reduced heteroaryl$C_{2-25}$alkyl or a substituted derivative of any of the foregoing groups, wherein the substituents are one or more independently of halogen, alkyl, halosubstituted alkyl, aryl, arylalkyl, heteroaryl, reduced heteroaryl, reduced heteroarylalkyl, arylalkoxy, cyano, nitro, —C(O)R⁴, —CO₂R⁵, —SOR⁴, —SO₂R⁴, —NR⁶R⁷, —OR⁶, —SR⁶, —C(O)CX¹X²NR⁶R⁷, —C(O)N(OH)R⁶, —C(O)NR⁵R⁴, —NR⁶C(O)R⁴, —CR⁶(NH₂)CO₂R⁶, —NHCX¹X²CO₂R⁶, —N(OH)C(O)NR⁶R⁷, —N(OH)C(O)R⁴, —NHC(O)NR⁶R⁷, —C(O)NHNR⁶R⁷, —C(O)N(OR⁵)R⁶, or a lipid or steroid (natural or synthetic) with the proviso that any hetero atom substituent in $R^1$ must be separated from the exocyclic sulphur atom by at least two carbon atoms (preferably saturated);
and where:
$R^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, —OR⁶, —NHCX¹X²CO₂R⁶ or —NR⁶R⁷;
$R^5$ is hydrogen, alkyl, alkenyl, alkynyl, cycloalkyl, cycloalkenyl, aryl, arylalkyl heteroaryl, heteroarylalkyl, reduced heteroaryl or reduced heteroarylalkyl; and
$R^6$ and $R^7$ are independently hydrogen, alkyl, alkenyl, alkynyl, cycloalkyl, cycloalkenyl, aryl, arylalkyl, heteroaryl, reduced heteroaryl, reduced heteroarylalkyl or —(CH₂)n(OR⁵)m wherein n is 1 to 12, preferably 2 to 10, wherein m is 1–3 and $R^5$ is most preferably $C_2$–$C_{10}$ alkyl; and
$X^1$ and $X^2$ are independently hydrogen, alkyl, alkenyl, alkynyl, cycloalkyl, cycloalkenyl, aryl, heteroaryl, arylalkyl, heteroarylalkyl, reduced heteroaryl or reduced heteroarylalkyl
with the proviso that when A is phenyl disubstituted at the 6 and 7 positions with methoxy groups, $R^1$ is not CH₂CH=CHPh.

In compounds of formula (Ia) any alkyl, alkenyl and alkynyl groups and moieties may be straight chain (unbranched) or branched chain. Straight chain alkyl, alkenyl and alkynyl groups or moieties may contain from 1 to 30 carbon atoms, eg. 1 to 25 carbon atoms, preferably 1 to 20 carbon atoms. Branched chain alkyl, alkenyl and alkynyl groups or moieties may contain from 1 to 50 carbon atoms, preferably 1 to 30 carbon atoms. It will be appreciated that alkenyl and alkynyl groups or moieties will contain at least 2 carbon atoms.

Preferred values for $R^1$, $R^4$, $R^5$, $R^6$, $R^7$, $X^1$ and $X^2$ are as defined below for formulae (IIa).

In this text, 'reduced', in the context of 'reduced heteroaryl' and the like means fully or partially saturated.

Aryl groups include for example optionally substituted unsaturated monocyclic or bicyclic rings of up to 12 carbon atoms, such as phenyl and naphthyl, and partially saturated bicyclic rings such as tetrahydro-naphthyl. Examples of substituents which may be present on an aryl group include one or more of halogen, amino, nitro, alkyl, haloalkyl, alkoxy, phenoxy and phenoxy substituted by one or more of halo, alkyl or alkoxy.

A heteroaryl group or moiety may be for example an optionally substituted 5- or 6-membered heterocyclic aromatic ring which may contain from 1 to 4 heteroatoms selected from O, N and S. The heterocyclic ring may optionally be fused to a phenyl ring. Examples of heteroaryl groups thus include furyl, thienyl, pyrrolyl, oxazolyl, oxazinyl, thiazolyl, imidazolyl, oxadiazolyl, thiadiazolyl, pyridyl, triazolyl, triazinyl, pyridazyl, pyrimidinyl, pyrazolyl, indolyl, indazolyl, benzofuranyl, benzothienyl, benzimidazolyl, benzoxazolyl, benzoxazinyl, quinoxalinyl, quinolinyl, quinazolinyl, cinnolinyl, benzothiazolyl, pyridopyrrolyl. Suitable substituents include one or more of halogen, oxo, amino, nitro, alkyl, haloalkyl, alkoxy, phenoxy and phenoxy substituted by one or more of halo, alkyl, haloalkyl or alkoxy.

A reduced heteroaryl group or moiety may be for example a fully or partially saturated derivative of the aforementioned heteroaryl groups. Examples of reduced heteroaryl groups thus include pyrrolidinyl, tetrahydrofuryl, tetrahydrothienyl and piperidinyl.

Preferably, a compound according to the second aspect of the invention is a compound of formula (IIa):

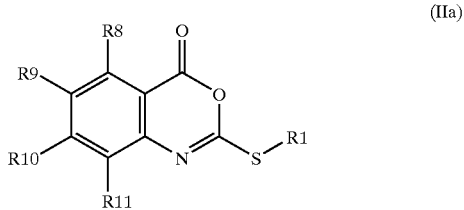

(IIa)

or a pharmaceutically acceptable salt, ester, amide or prodrug therof,
wherein:
$R^1$, $R^4$, $R^5$, $R^6$, $R^7$, $X^1$ and $X^2$ are as defined above for formula (Ia); and
$R^8$, $R^9$, $R^{10}$, $R^{11}$ are each independently hydrogen, halo, hydroxy, amino, nitro, cyano,
or a group $R^1$, as defined above,
or a group $R^{12}Q$ where Q is O, CO, CONH, NHCO, S, SO, $SO_2$, or $SO_2NH^2$ and $R^{12}$ is hydrogen or a group $R^1$ as defined above, with the proviso that when $R^1$ is $CH_2CH=CHPh$, $R^8$ and $R^{11}$ are H and $R^9$ is OMe, $R^{10}$ is not OMe,
or a group $R^1R^2N$ where $R^1$ is as defined above and $R^2$ is hydrogen or $R^1$, with the proviso that any hetero atom substituent in $R^1$ and/or $R^2$ must be separated from the nitrogen atom substituent by at least two carbon atoms (preferably saturated).

More preferably, a compound according to the first aspect of the invention comprises a compound of formula (IIa), or a pharmaceutically acceptable salt, ester, amide or prodrug therof; wherein:
$R^1$ is a unbranched alkyl group having from 3 to 25 carbon atoms; an aryl group; an arylalkyl group wherein the alkyl moiety has from 2 to 25 carbon atoms; or an arylaryl group, wherein the arylalkyl group or the arylaryl group may be separated by a spacer, and where the spacer can be one or more of an ester, amide, O, $CH_2$ or a ketone;
$R^8$ is hydrogen or fluorine;
$R^9$ is lower branched or unbranched alkyl having 1 to 10 carbon atoms, preferably methyl; cyclic alkyl having 3 to 10 carbon atoms, preferably cyclopropyl; haloalkyl, preferably trifluoromethyl; or a halogen, most preferably chlorine or fluorine;
$R^{10}$ is hydrogen lower branched or unbranched alkyl having 1 to 10 carbon atoms, preferably methyl; cyclic alkyl having 3 to 10 carbon atoms, preferably cyclopropyl; haloalkyl, preferably trifluoromethyl; or a halogen, most preferably chlorine or fluorine;
$R^{11}$ is hydrogen lower branched or unbranched alkyl having 1 to 10 carbon atoms, preferably methyl, or halogen, preferably fluorine.

In particular, $R^1$ is an unbranched alkyl with 8, 9, 10, 11, 12, 13, 14, 15, 16, 17, 18, 19 or 20 carbon atoms, a phenyl group, a phenylalkyl group wherein the alkyl is an unbranched group containing from 2 to 20 carbon atoms for example 8 to 20 carbon atoms, or a phenoxyphenyl group,
wherein the phenyl group is optionally substituted with methyl, halide or halomethyl where the halide is F, Cl, Br or I,
$R^8$ is hydrogen and $R^9$, $R^{10}$ and $R^{11}$ are independently H or methyl
or one of $R^8$, $R^9$, $R^{10}$ or $R^{11}$ is methyl and the others of $R^8$, $R^9$, $R^{10}$ and $R^{11}$ are hydrogen,
in particular, $R^8$ is hydrogen and one of $R^9$, $R^{10}$ and $R^{11}$ is methyl and the others of $R^9$, $R^{10}$ and $R^{11}$ are hydrogen.

Examples of pharmaceutically acceptable salts of the compounds of formulae (I), (Ia) and (IIa) include those derived from organic acids such as methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of formula (I), (Ia) or (IIa) contains an acidic function a base salt of said compound may be prepared by reacting said compound with a suitable base. The acid or base salt may separate directly or can be obtained by concentrating the solution eg. by evaporation. The compounds of this invention may also exist in solvated or hydrated forms.

The invention also extends to prodrugs of the aforementioned compounds. A prodrug is commonly described as an inactive or protected derivative of an active ingredient or a drug which is converted to the active ingredient or drug in the body.

Representative compounds according to the first aspects of the invention include:

TABLE 1

| Reference Number | Structure | Compound Name |
|---|---|---|
| 1 | 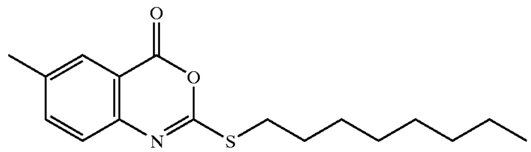 | 6-Methyl-2-octylthio-4H-3,1-benzoxazin-4-one |
| 2 | 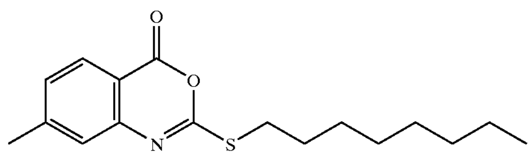 | 7-Methyl-2-octylthio-4H-3,1-benzoxazin-4-one- |
| 3 | 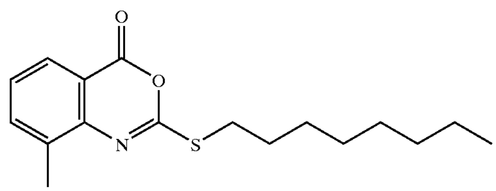 | 8-Methyl-2-octylthio-4H-3,1-benzoxazin-4-one |
| 4 | 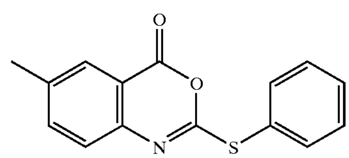 | 6-Methyl-2-phenylthio-4H-3,1-benzoxazin-4-one |
| 5 | 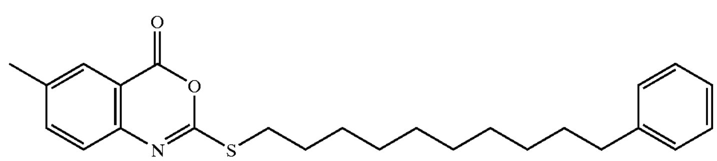 | 6-Methyl-2-(10-phenyldecyl)-thio-4H-3,1-benzoxazin-4-one |
| 6 | 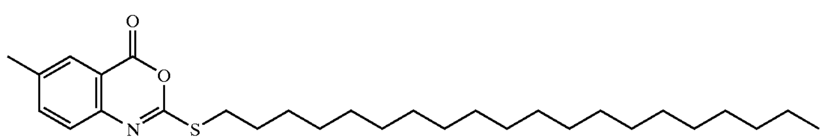 | 6-Methyl-2-icosylthio-4H-3,1-benzoxazin-4-one |
| 7 | 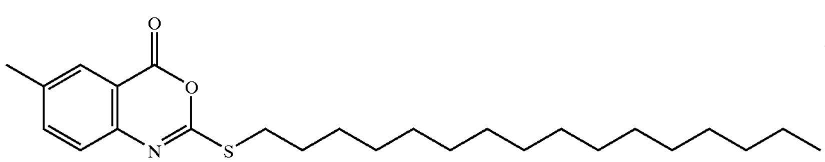 | 6-Methyl-2-hexadecylthio-4H-3,1-benzoxazin-4-one |

Preferred compounds of the invention listed above extend to the tautomers thereof, as well as (but not limited to) pharmaceutically acceptable salts, esters, amides or pro-drugs thereof or a derivative optionally with one or more lipid groups (natural or synthetic) attached.

All preferred features of the first aspect of the invention also apply to the second aspect.

A third aspect of the invention provides a process for the manufacture of any one or more of the novel compounds or derivatives according to the first or second aspects of the invention. Thus, the present invention provides a process for the preparation of a novel compound of formula (II) which process comprises:

Process (A) reacting a compound of formula (IV):

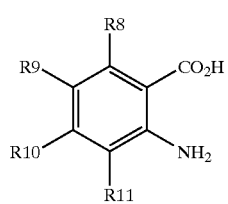

(IV)

with a compound of formula (V):

(V)

or

Process (B) cyclising a compound of formula (VI)

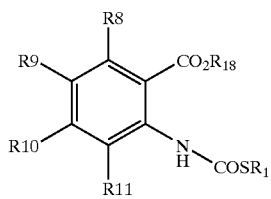

(VI)

wherein $R^1$ and $R^8$–$R^{11}$ are as hereinbefore defined and $R^{18}$ is hydrogen or $C_{1-6}$alkyl.

or:

Process (C) reacting a compound of formula (VII)

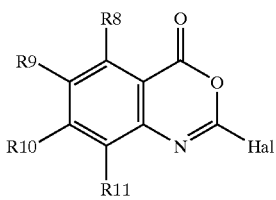

(VII)

with a thiol of formula (VIII):

SH      (VIII)

or:

Process (D): reacting a compound of formula (IX):

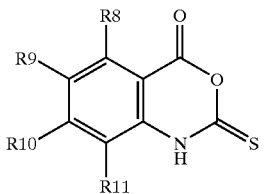

(IX)

with a compound of formula (X):

$R^1$      (X)

or:

Process (E) converting a compound of formula (Ia) or (IIa) into a different compound of formula (Ia) or (IIa), by, for example,
(i) reduction of a compound of formula (Ia) or (IIa) wherein any of $R^1$, $R^8$, $R^9$, $R^{10}$ and $R^{11}$ contains an alkenyl or alkynyl group or moiety, to the corresponding alkyl or alkenyl group or moiety; or
(ii) alkylation of a compound of formula (Ia) or (IIa) where one or more of $R^8$, $R^9$, $R^{10}$ and $R^{11}$ represents a halogen atom.

Process (A) may be effected by reacting a compound of formula (IV) with a chlorothiolformate of formula (V). The process is preferably carried out under basic conditions, e.g. using pyridine. An excess (more than two equivalents) of the chlorothiolformate is employed, so that the intermediate thiolcarbamate initially formed is cyclised by reaction with the excess chlorothiolformate.

Compounds of formula (V) for use in the process (A) may be prepared by standard methods well known in the art, e.g. by reaction of the corresponding thiol $R^1SH$ with phosgene.

Process (B) may be effected by reaction of a compound (VI) wherein $R^{18}$ is hydrogen, in the presence of a cyclisation reagent, e.g. an alkyl chloroformate, for example as described for process (A). Alternatively a compound (VI) may be cyclised by treatment with a dehydrating agent such as concentrated sulphuric acid.

Compounds of formula (VI) may be prepared by reacting a compound of formula (IV) or a corresponding ester with chlorothiolformate. It will be appreciated that when an acid of formula (IV) is employed the thiolformate should not be used in excess, otherwise cyclisation will occur as in Process (A). However where an ester of formula (IV) is employed an excess of the thiolformate may be employed, and indeed it may be advantageous to do so.

Alternatively, compounds (VI) wherein $R^{18}$ is an alkyl group may be prepared by reacting an ester corresponding to formula (IV) with e.g. phosgene and a base such as pyridine to afford the corresponding isocyanate, followed by treatment with an alcohol $R^1SH$. If desired the ester (i.e. where $R^{18}$ is alkyl) may be hydrolysed to the corresponding acid ($R^{18}$=H) using for example lithium hydroxide in e.g. aqueous tetrahydrofuran or aqueous dioxane.

It will be appreciated that process (A) also proceeds via an intermediate of formula (VI) and is hence a variant of process (B).

Process (C) may be effected by reacting a compound of formula (VII) with a thiol of formula (VIII) in the presence of a base such as triethylamine.

Process (D) may be effected by reacting a compound of formula (IX) with an alkyl iodide and potassium carbonate in a solvent such as acetone.

A compound of formula (IX) may be prepared by cyclisation of a compound of formula (IV), with thiophosgene. (See Krantz et al., *J. Med. Chem.* 1990, 33(2):464–479).

In process (E), reduction of an alkenyl or alkynyl group may be effected for example by catalytic hydrogenation using e.g. 10% palladium on charcoal in an alcoholic solvent, such as ethanol, under 1 atmosphere of hydrogen gas.

Alkylation according to process (E)(ii) may be effected using a Stille or other palladium catalysed cross-coupling process, using e.g. tetra-alkyl tin such as tetramethyl tin and $PhCH_2Pd(PPh_3)_2Cl$ in HMPA at elevated temperature e.g. 50–100° C. Other halides or pseudohalides e.g. triflates may be employed as starting materials.

A fourth aspect of the invention is a novel compound according to the first and/or second aspects of the invention (i.e. compounds of formulae (Ia) and (IIa)), for use in medicine. Preferred features of the first and/or second aspects of the invention also apply to the fourth aspect. Further details of the fourth aspect of the invention are set out in the text which follows.

The compounds of formula (Ia) and (IIa) are useful inhibitors of enzymes involved in the degradation of fats. Preferably therefore the fourth aspect of the invention provides a compound of formula (Ia) or (IIa) as defined hereinabove, or a pharmaceutically acceptable salt, ester, amide or prodrug thereof, for use in the control or treatment of obesity, or obesity-related disorders or for use in promoting non-medical weight loss.

A fifth aspect of the invention relates to a compound according to the first and/or second aspects of the invention for use in the inhibition of an enzyme whose preferred mode of action is to catalyse the hydrolysis of an ester functionality. This includes both in vivo and in vitro uses and other uses such as industrial uses. Such an enzyme is one which catalyses the breakdown of a substrate containing an ester functionality by the addition of water, resulting in the cleavage of a chemical bond. Such enzymes are involved in key processes in the body. Enzymes according to this invention include lipases (hydrolyse fatty acid esters), esterases (hydrolyse esters) and phosphatases (hydrolyse phosphate esters).

The enzyme is preferably a lipase. Lipases include pancreatic lipase, gastric lipase, lipoprotein lipase, lingual lipase, adipose tissue lipase, hormone sensitive lipase, phospholipase A1, A2, B, C, D etc., hepatic lipase, and other triacyl, diacyl and monoacylglycerol lipases in the mammalian body. Many similar such lipases are also known in plants, fungi and microorganisms.

Also covered are esterase enzymes and phosphatase enzymes. Esterase enzymes include pig liver esterase, cholesteryl esterase, retinyl esterase, 1-alkyl-2-acetylglycerophosphocholine esterase, carboxylic ester hydrolases, and cholesterol esterase. Phosphatase enzymes include serine/threonine phosphatases PP1, PP2 and PP3, phosphoprotein phosphatase, myosin-light-chain phosphatase, protein phosphoprotein 2C, and protein tyrosine phosphatase.

Compounds according to the invention, for use in medicine, are primarily for use in relation to the prevention and/or treatment of a medical condition such as obesity, hyperlipaemia, hyperlipidaemia and related diseases such as hyperglycaemia (type II diabetes), hypertension, cardiovascular disease, stroke, gastrointestinal disease and gastrointestinal conditions. Compounds according to the first aspect of the invention are useful in these and other conditions due to their ability to inhibit an enzyme whose preferred mode of action is to catalyse the hydrolysis of an ester functionality (in vivo, as the enzyme naturally occurs). The invention also relates to non-medical weight loss, such as cosmetic weight loss and includes improving bodily appearance in general. Throughout this text, the prevention and/or treatment of any disorder means any effect which mitigates any damage or any medical disorder, to any extent, and includes prevention and treatment themselves. The term "treatment" means any amelioration of disorder, disease, syndrome, condition, pain or a combination of two or more thereof.

Preferably therefore the invention provides the use of a compound of formula (I) or (II) as defined hereinabove, or a pharmaceutically acceptable salt, ester, amide or prodrug thereof, in the manufacture of a medicament for the control or treatment of obesity, or obesity-related disorders or for promoting non-medical weight loss.

Clearly, an important application of the invention is in relation to weight loss (of all kinds as described above) in humans. However, the invention applies to medical and non-medical weight loss in any animal whose metabolism of fat and fat derivatives involves an enzyme whose preferred mode of action is to catalyse the hydrolysis of an ester functionality (in vivo, as the enzyme naturally occurs). Thus, the invention has veterinary application and is particularly useful in relation to medical and non-medical weight loss in companion animals such as pet cats and dogs as well as in animals which provide meat for human consumption. In the case of the latter, the application of the present invention is to reduce fat content in order to provide a leaner meat product.

It is also believed that the compounds may be useful in reducing levels of toxins (e.g. dioxins and PCBs) stored in body fat. Without wishing to be bound by theory, it is believed that increasing the amount of undigested fat passing through the body enhances diffusion of toxins from fat stored in the body into fats in the blood, and thence into the intestine.

The fifth aspect of the invention has important applications. It includes test and diagnostic methods and the control and inhibition of unwanted enzymes, preferably lipases, in any process or in any product. The processes or products, which preferably involve a lipase, include: processing of agricultural commodities (e.g. oilseeds), recovery and isolation of enzymes from biotechnological processes (e.g. involving lysis of microorganisms), the manufacture and extraction of crude oil (especially oil and plastics), the industrial manufacture of triglycerides or other fats, manufacture of healthcare goods which comprise surfactants, soap or detergent (e.g. bath oils, creams), the manufacturing and processing of liposomes (e.g. healthcare products, diagnostics, gene therapy), the treatment of industrial waste (e.g. paper effluent treatment) and preventing the degradation of foodstuff which comprises a fat (e.g. chocolate processing). Thus, the invention also relates to these products and processes, e.g. a foodstuff which comprises a compound according to the first aspect of the invention, in particular foodstuffs which have a high fat content such as cakes, biscuits, pastry-products and the like and chocolate products. The preferred features of the fifth aspect of the invention, including an enzyme whose preferred mode of action is to catalyse the hydrolysis of an ester functionality (in vivo, as the enzyme naturally occurs) are as discussed for the previous aspects of the invention.

A sixth aspect of the invention provides a composition comprising a novel compound according to the first or second aspect of the invention, in combination with a pharmaceutically acceptable carrier or diluent. Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The compounds according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the compounds can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises ail aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The compositions of the sixth aspect of the invention are useful in the prevention and/or treatment of obesity, obesity-related disorder, other medical weight loss and non-medical related weight loss. Preferred features of this aspect of the invention are as described above for the first to fifth aspects of the invention.

A seventh aspect of the invention provides a process for the manufacture of a composition according to the sixth aspect of the invention. The manufacture can be carried out by standard techniques well known in the art and involves combining a compound according to the first aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

An eighth aspect of the invention provides a method for the prevention and/or treatment of obesity or an obesity-related disorder, the method comprising the administration of a compound according to the first or second aspect of the invention, preferably in combination with a pharmaceutically acceptable carrier or diluent (as per the sixth aspect of the invention). Obesity-related disorders include hyperlipeamia, hyperlipideamia, hyperglycaemia, hypertension, cardiovascular disease, stroke, gastrointestinal disease and gastrointestinal conditions. The compound or composition is preferably administered to a patient in need thereof and in a quantity sufficient to prevent and/or treat the symptoms of the condition, disorder or disease. For all aspects of the invention, particularly medical ones, the administration of a compound or composition has a dosage regime which will ultimately be determined by the attending physician and will tale into consideration such factors such as the compound being used, animal type, age, weight, severity of symptoms, method of administration, adverse reactions and/or other contraindications. Specific defined dosage ranges can be determined by standard design clinical trials with patient progress and recovery being fully monitored. Such trials may use an escalating dose design using a low percentage of the maximum tolerated dose in animals as the starting dose in man.

The physiologically acceptable compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

A ninth aspect of the invention provides a cosmetic method (non-therapeutic) for maintaining a given weight, or for cosmetic weight loss, the method comprising the administration of a compound according to the first or second aspect of the invention, preferably in combination with a pharmaceutically acceptable carrier or diluent (as per the sixth aspect of the invention). The compound or composition is preferably administered to a subject in need thereof or having a requirement therefor and in a quantity sufficient to maintain a given weight or for cosmetic weight loss.

The eighth and ninth aspects of the invention relate to methods which are applicable to humans and other animals, in particular companion animals (such as dogs and cats) and other animals which provide meat for human consumption, such as cattle, pigs and sheep (all of any age).

The invention will now be described with reference to the following non-limiting examples.

Biological Test Methods and Results

Test Compounds

The benzoxazinone compounds used in the following tests are identified by the reference number assigned in Table 1 hereinbefore.

Measurement of Lipase Activity Using a Quinine Diimine Dye Colorimetric Assay

The inhibitory activity of the selected compounds to pancreatic lipase was measured in the following assay available from Sigma Ltd (Lipase-PS™, catalog number 805-A):

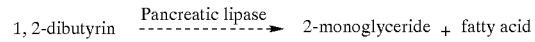

17

-continued

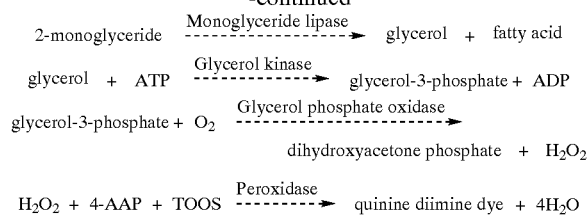

The glycerol released from the action of pancreatic and monoglyceride lipase was oxidised to release $H_2O_2$. The peroxidase reaction step then produces a quinine dye which is pink in colour and absorbs light at a wavelength of 550 nm.

Inhibitor

Individual test compounds were dissolved in DMSO (dimethyl sulphoxide) at 10 mM. DMSO was used to avoid any problems with compounds being water-insoluble.

For individual compounds, the $IC_{50}$ (concentration at which lipase activity is inhibited to one half of the maximum) was calculated by measuring the inhibitory activity from log-dose response curves using a range of inhibitor concentrations.

Results

Compounds 1, 2, 3, 5, 6 and 7 were assayed in the quinine diimine dye colorimetric assay which provides a rapid method to measure lipase inhibitory activity. None of the compounds tested interfered with the colorimetric reaction, i.e. they did not give false positive results.

A range of inhibitory activities for the tested compounds was observed, indicating that these compounds are inhibitors of human pancreatic lipase. Compounds 1, 2, 3, 5, 6 and 7 all had an $IC_{50}$ of <100 nM.

Measurement of Lipase Enzyme Activity Using a NaOH Titration Method

The inhibitory activity of the selected compounds to pancreatic lipase was measured in the assay described in Pasquier et al; 1996, Vol 7, *Nutritional Biochemistry*, 293–302.

Log dose/response curves were constructed using a range of inhibitor concentrations.

Results

Selected benzoxazinone compounds were tested in the NaOH titration assay. In this assay, the activity of porcine pancreatic lipase in a system containing lipid micelles is recorded. These conditions are therefore similar to those encountered in the gastrointestinal tract.

A range of inhibitory activities were observed for the tested benzoxazinone compounds in this assay, indicating that these compounds are inhibitors of porcine pancreatic lipase. Compounds 4 and 5 had an $IC_{50}$ of less than 1 microMolar.

The results demonstrate that a number of selected benzoxazinones are inhibitors of fat digestion and that these compounds may be particularly suitable for the treatment of obesity.

Synthesis of Novel Compounds According to the Invention

18

EXAMPLE 1

Preparation of 2-octylthio-6-methyl-4H-3,1-benzoxazin-4-one

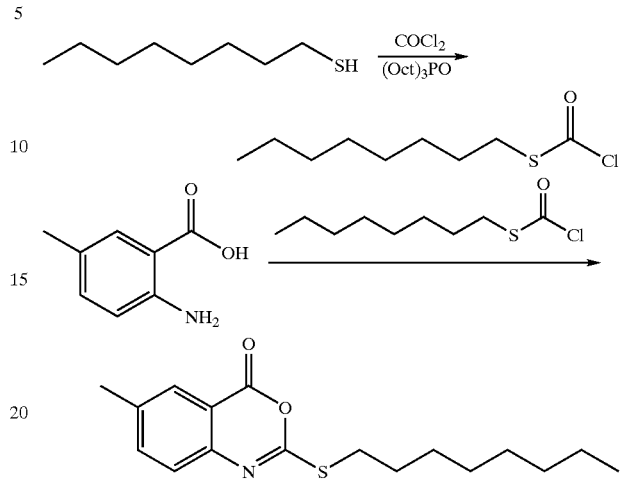

(a) 1-Octanethiol (5 ml, 28 mmol) and trioctylphosphine oxide (22 mg, 0.056 mmol) were heated to 80° C. Phosgene solution (20% in PhMe, 14.4 ml, 30 mmol) was added portionwise over the course of 1 hour, then the reaction was maintained at 80° C. for a further 1 hour. After allowing to cool to room temperature, hydrogen chloride and excess phosgene were removed overnight under a gentle stream of nitrogen, the vented gas being passed through a sodium hydroxide scrubber. The crude octyl chlorothiolformate was used directly in the next step.

(b) 2-Amino-5-methylbenzoic acid (1.51 g, 10 mmol) was dissolved in pyridine (10 ml), and to this was added the crude octyl chlorothiolformate (28 mmol, assuming 100% from the first step) as a solution in toluene. After 2 h, the reaction was diluted with ethyl acetate and washed three times with 1M aqueous HCl, then saturated aqueous sodium bicarbonate, water and brine. The organic phase was dried ($MgSO_4$) and concentrated in vacuo. Crystallisation from hexane gave the title compound (155 mg, 5%): $\delta_H$ (400 MHz, $CDCl_3$) 0.91 (3H, t, J 7.0, Me), 1.30–1.34 (8H, m, 4×$CH_2$), 1.44–1.50 (2H, m, $SCH_2CH_2CH_2$), 1.79 (2H, qn, J 7.4, $SCH_2CH_2$), 2.46 (3H, s, ArMe), 3.16 (2H, t, J 7.3, $SCH_2$), 7.38 (1H, d, J 8.2, ArH), 7.58 (1H, dd, J 8.2, 1.8, ArH), 7.93 (1H, s, ArH); m/z ($ES^+$) 306 ($MH^+$).

EXAMPLE 2

Preparation of 2-octylthio-7-methyl-4H-3,1-benzoxazin-4-one

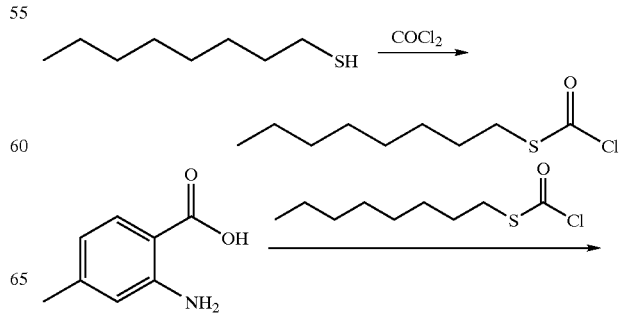

19

-continued

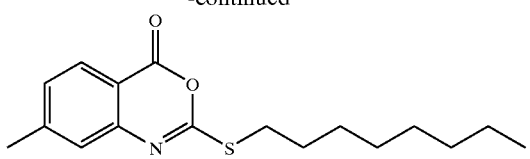

1-Octanethiol (0.71 ml, 4.1 mmol) was dissolved in THF (10 ml). To this solution was added a solution of phosgene (20% in PhMe, 3.5 ml, 7.4 mmol). After 2.5 h the reaction vessel was purged with nitrogen to remove excess phosgene and hydrogen chloride, the vented gas being passed through a scrubber containing dilute aqueous sodium hydroxide. The crude octyl chlorothiolformate solution was used directly. 2-Amino-4-methylbenzoic acid (151 mg, 1 mmol) was dissolved in pyridine (0.5 ml) and DCM (5 ml). To this was added one quarter of the crude octyl chlorothiolformate solution (1 mmol, assuming 100% from the first step). After 24 h, the reaction was diluted with ether and washed with 1M aqueous HCl and brine. The organic phase was dried (MgSO$_4$) and concentrated in vacuo. The residue was purified by flash chromatography (EtOAc/hexane gradient) to give a solid which was triturated with acetonitrile to afford the title compound (43 mg, 14%): δ$_H$ (400 MHz, CDCl$_3$) 0.82 (3H, t, J 6.7, Me), 1.21–1.24 (8H, m, 4×CH$_2$), 1.37–1.41 (2H, m, SCH$_2$CH$_2$CH$_2$), 1.68–1.72 (2H, m, SCH$_2$CH$_2$), 2.40 (3H, s, ArMe), 3.08 (2H, t, J 7.4, SCH$_2$), 7.16 (1H, d, J 8.0, ArH), 7.19 (1H, d, J 1.4, ArH), 7.93 (1H, d, J 8.0, ArH); m/z (ES$^+$) 306 (MH$^+$).

EXAMPLE 4

Preparation of 2-phenylthio-6-methyl-4H-3,1-benzoxazin-4-one

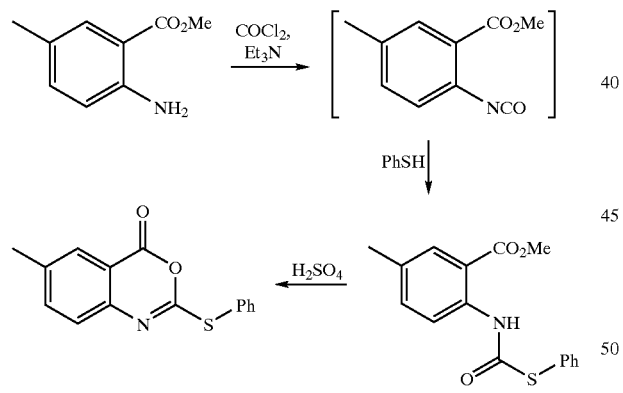

2-Amino-5-methylbenzoic acid methyl ester (122 mg, 0.79 mmol) and triethylamine (0.28 ml, 1.96 mmol) were dissolved in THF (10 ml). A 20% solution of phosgene in toluene (0.74 ml, 1.6 mmol) was added, causing immediate formation of a white precipitate. After 1 h, excess phosgene was purged with a stream of nitrogen, the vented gas being passed through a base scrubber. Thiophenol (81 μl, 0.79 mmol) was added to this crude isocyanate solution, which was then stirred for 1 h. The mixture was filtered to remove triethylamine hydrochloride, the solid being washed with ether. After concentration of the filtrate, the residue was purified by flash chromatography (5% to 10% EtOAc/petrol) to give 5-methyl-2-phenylsulfanylcarbonylaminobenzoic acid, methyl ester: m/z (ES$^+$) 300 (M–H).

A portion of this material (82 mg, 0.27 mmol) was cyclised by dissolving it in concentrated sulfuric acid (5 ml). After 2.5 h, the mixture was poured carefully onto a mixture of ice and aqueous sodium bicarbonate, with further portions of solid sodium carbonate being added periodically to avoid the mixture becoming acidic. The resulting mixture was extracted with ethyl acetate, the organic phase then being dried (MgSO$_4$) and concentrated to afford the title compound (64 mg, 0.24 mmol, 87%) as a yellow solid, which did not require further purification: δ$_H$ (400 MHz, CDCl$_3$) 2.35 (3H, s, ArMe), 7.20 (1H, d, J 8.5, ArH), 7.39–7.46 (4H, m, ArH), 7.58–7.60 (2H, m, ArH), 7.82 (1H, s, ArH); m/z (ES$^+$) 270.2 (MH$^+$).

The foregoing description details specific compounds, compositions, methods and uses which can be employed to practice the present invention. However, those skilled in the art will know how to use alternative reliable methods for aiming at alternative embodiments of the invention which are herein encompassed.

What is claimed is:

1. A compound of formula (Ia):

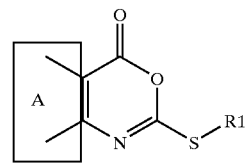

(Ia)

or a pharmaceutically acceptable salt, ester, amide or prodrug thereof;

wherein in formula (Ia):

A is a 6-membered aromatic ring optionally substituted with one or more groups as defined below for R$^1$; and R$^1$ is a branched C$_{4-50}$alkyl or unbranched C$_{3-25}$alkyl, a branched C$_{4-50}$alkylether or unbranched C$_{3-25}$alkylether, a branched C$_{4-50}$alkylpolyether or unbranched C$_{3-25}$alkylpolyether, C$_{2-25}$alkenyl, C$_{2-25}$alkynyl, C$_{3-10}$cycloalkyl, C$_{3-10}$cyclonalkenyl, aryl, arylC$_{2-25}$alkyl, reduced arylC$_{1-25}$alkyl, arylC$_{2-25}$alkenyl, heteroaryl, heteroarylC$_{2-25}$alkyl, heteroarylC$_{2-25}$alkenyl, reduced aryl, reduced heteroaryl, reduced heteroarylC$_{2-25}$alkyl or a substituted derivative of any of the foregoing groups, wherein the substituents are one or more independently of halogen, alkyl, halosubstituted alkyl, aryl, arylalkyl, heteroaryl, reduced heteroaryl, reduced heteroarylalkyl, arylalkoxy, cyano, nitro, —C(O)R$^4$, —CO$_2$R$^5$, —SOR$^4$, —SO$_2$R$^4$, —NR$^6$R$^7$, —OR$^6$, —SR$^6$, —C(O)CX$^1$X$^2$NR$^6$R$^7$, —C(O)N(OH)R$^6$, —C(O)NR$^5$R$^4$, —NR$^6$C(O)R$^4$, —CR$^6$(NH$_2$)CO$_2$R$^6$, —NHCX$^1$X$^2$CO$_2$R$^6$, —N(OH)C(O)NR$^6$R$^7$, —N(OH)C(O)R$^4$, —NHC(O)NR$^6$R$^7$, —C(O)NHNR$^6$R$^7$, —C(O)N(OR$^5$)R$^6$ with the proviso that any hetero atom substituent in R$^1$ must be separated from the exocyclic sulphur atom by at least two carbon atoms;

and where:

R$^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, —OR$^6$, —NHCX$^1$X$^2$CO$_2$R$^6$ or —NR$^6$R$^7$;

R$^5$ is hydrogen, alkyl, alkenyl, alkynyl, cycloalkyl, cycloalkenyl, aryl, arylalkyl heteroaryl, heteroarylalkyl, reduced heteroaryl or reduced heteroarylalkyl;

R⁶ and R⁷ are independently hydrogen, alkyl, alkenyl, alkynyl, cycloalkyl, cycloalkenyl, aryl, arylalkyl, heteroaryl, reduced heteroaryl, reduced heteroarylalkyl or —(CH₂)ₙ(OR⁵)ₘ wherein n is 1 to 12, wherein m is 1 to 3; and X¹ and X² are independently hydrogen, alkyl, alkenyl, alkynyl, cycloalkyl, cycloalkenyl, aryl, heteroaryl, arylalkyl, heteroarylalkyl, reduced heteroaryl or reduced heteroarylalkyl with the proviso that when A is phenyl disubstituted at the 6 and 7 positions with methoxy groups, R¹ is not CH₂CH=CHPh.

2. A compound according to claim 1 of formula (IIa):

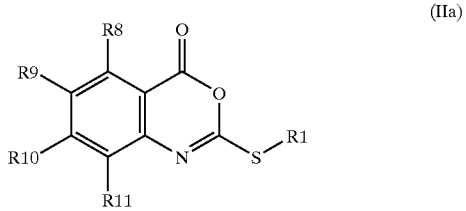

(IIa)

or a pharmaceutical salt, ester, amide or prodrug thereof,
wherein:

R¹, R⁴, R⁵, R⁶, R⁷, X¹ and X² are as defined in claim 1 for formula (Ia); and

R⁸, R⁹, R¹⁰, R¹¹ are each independently hydrogen, halo, hydroxy, amino, nitro, cyano, or a group R¹, as defined in claim 1 for formula (Ia), or a group R¹²Q where Q is O, CO, CONH, NHCO, S, SO, SO₂, or SO₂NH₂ and R¹² is hydrogen or a group R¹ as defined in claim 1 for formula (Ia) with the proviso that when R¹ is CH₂CH=CHPh, R⁸ and R¹¹ are H and R⁹ is OMe; R¹⁰ is not OMe, or a group R¹R²N where R¹ is as defined in claim 1 for formula (Ia) and R² hydrogen or R¹, with the proviso that any hetero atom substituent in R¹ and/or R² must be separated from the nitrogen atom substituent by at least two carbon atoms.

3. A compound according to claim 2, wherein R¹ is a unbranched alkyl group having from 3 to 25 carbon atoms; an aryl group; an arylalkyl group wherein the alkyl moiety has from 2 to 25 carbon atoms; or an arylaryl group, wherein the arylalkyl group or the arylaryl group maybe separated by a spacer, and where the spacer can be one or more of an ester, amide, O, CH₂ or a ketone;

R⁸ is hydrogen or fluorine;

R⁹ is lower branched or unbranched alkyl having 1 to 10 carbon atoms; cyclic alkyl having 3 to 10 carbon atoms; haloalkyl; or a halogen;

R¹⁰ is hydrogen lower branched or unbranched alkyl having 1 to 10 carbon atoms; cyclic alkyl having 3 to 10 carbon atoms; haloalkyl; or a halogen; and R¹¹ is hydrogen lower branched or unbranched alkyl having 1 to 10 carbon atoms or a halogen.

4. A compound as claimed in claim 2, or a pharmaceutically acceptable salt, ester, amide or prodrug thereof wherein:

R¹ is an unbranched alkyl with 8, 9, 10, 11, 12, 13, 14, 15, 16, 17, 18, 19 or 20 carbon atoms, a phenyl group, a phenylalkyl group wherein the alkyl is an unbranched group containing from 2 to 20 carbon atoms, or a phenoxyphenyl group, wherein the phenyl group is optionally substituted with methyl, halide or halomethyl where the halide is F, Cl, Br or I, R⁸ is hydrogen, and R⁹, R¹⁰ and R¹¹ are independently H or methyl.

5. A compound selected from the group consisting of:

6-Methyl-2-octylthio-4H-3,1-benzoxazin-4-one;

7-Methyl-2-octylthio-4H-3,1-benzoxazin-4-one;

8-Methyl-2-octylthio-4H-3,1-benzoxazin-4-one;

6-Methyl-2-phenylthio-4H-3,1-benzoxazin-4-one;

6-Methyl-2-(10-phenyldecyl)thio-4H-3,1-benzoxazin-4-one;

6-Methyl-2-icosylthio-4H-3,1-benzoxazin-4-one;

6-Methyl-2-hexadecylthio-4H-3,1-benzoxazin-4-one;

pharmaceutically acceptable salts thereof, esters thereof, amides thereof and prodrugs thereof.

6. A process for the preparation of a compound of formula (Ia) or (IIa) which process is selected from the group consisting of:

Process (A): reacting a compound of formula (IV):

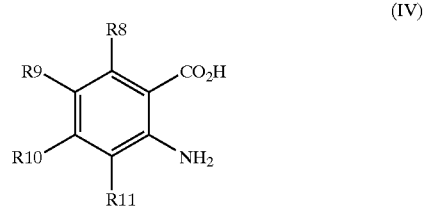

(IV)

with a compound of formula (V):

(V)

wherein R¹ and R⁸–R¹¹ are as defined in claim 2 for formula (IIa);

Process (B): cyclising a compound of formula (VI):

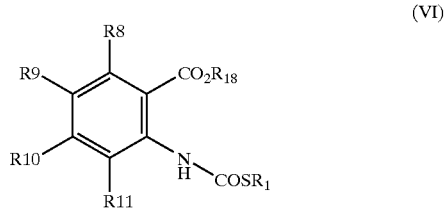

(VI)

wherein R¹ and R⁸–R¹¹ are as defined in claim 2 for formula (IIa) and R¹⁸ is hydrogen or C₁₋₆alkyl;

Process (C): reacting a compound of formula (VII):

$$\text{(VII)}$$

with a thiol of formula (VIII):

$$R^1SH \quad \text{(VIII)}$$

wherein $R^1$ and $R^8$–$R^{11}$ are as defined in claim 2 for formula 2 (IIa);

Process (D): reacting a compound of formula (IX):

$$\text{(IX)}$$

with a compound of formula (X):

$$ICH_2R^1 \quad \text{(X)}$$

wherein $R^1$ and $R^8$–$R^{11}$ are as defined in claim 2 for formula (IIa);

Process (E): converting a compound of formula (Ia) or (IIa) into a different compound of formula (Ia) or (IIa), by a process selected from the group consisting of:
  (i) reduction of a compound of formula (Ia) or (IIa) wherein any of $R^1$, $R^8$, $R^9$, $R^{10}$ and $R^{11}$ contains an alkenyl or alkynyl group or moiety, to the corresponding alkyl or alkenyl group or moiety; and
  (ii) alkylation of a compound of formula (Ia) or (IIa) where one or more $R^8$, $R^9$, R10 and $R^{11}$ represents a halogen atom.

7. A pharmaceutical composition comprising the compound of any one of claims 1 to 5 or a pharmaceutically acceptable salt, ester, amide or pro-drug thereof, in combination with a pharmaceutically acceptable carrier or diluent.

8. The composition of claim 7, wherein the compound is present in an amount sufficient to inhibit an enzyme whose preferred mode of action is to catalyse the hydrolysis of an ester functionality.

9. The composition of claim 8 wherein the compound is present in an amount sufficient to treat obesity or a disorder caused by obesity selected from hyperlipaemia, hyperlipidaemia, hyperglycaemia (type II diabetes), hypertension, cardiovascular disease, stroke, gastrointestinal disease and gastrointestinal conditions.

10. The composition of claim 7 wherein the compound is present in an amount sufficient to reduce levels of toxins in body fat.

11. The composition of claim 7 wherein the composition is formulated for administration to humans.

12. The composition of claim 7 wherein the composition is formulated for administration to animals.

13. A food product comprising a compound of formula (Ia) or (IIa) as defined in any one of claims 1 to 5 or a pharmaceutically acceptable salt, ester, amide or pro-drug thereof.

14. A method for inhibiting an enzyme whose preferred mode of action is to catalyse the hydrolysis of an ester functionality comprising contacting the enzyme with a compound of formula (Ia) or (IIa) as defined in any one of claims 1 to 5 or a pharmaceutically acceptable salt, ester, amide, or pro-drug thereof.

15. The method of claim 14, wherein the step of contacting the compound with the enzyme controls and inhibits unwanted enzymes in a process or product.

16. A process for preparing a pharmaceutical composition comprising:
  providing a compound of any one of claims 1 to 5 or a pharmaceutically acceptable salt, ester, amide or pro-drug thereof; and
  mixing the compound or pharmaceutically acceptable salt, ester, amide or pro-drug thereof with a pharmaceutically acceptable carrier or diluent.

17. A method for the prevention or treatment of obesity or a disorder caused by obesity, the method comprising administering to a patient a compound of formula (I);

$$\text{(I)}$$

or a pharmaceutically acceptable salt, ester, amide or pro-drug thereof,
  wherein in formula (I):
  A is a 6-membered aromatic ring optionally substituted with one or more groups as defined below for $R^1$; and
  $R^1$ is a branched or unbranched alkyl, a branched or unbranched alkylether, a branched or unbranched alkylpolyether, alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups, wherein the substituents are one or more independently of halogen, alkyl, halosubstituted alkyl, aryl, arylalkyl, heteroaryl, reduced heteroaryl, reduced heteroarylalkyl, arylalkoxy, cyano, nitro, —C(O)R$^4$, —CO$_2$R$^5$, —SOR$^4$, —SO$_2$R$^4$, —NR$^6$R$^7$, —OR$^6$, —SR$^6$, —C(O)CX$^1$X$^2$NR$^6$R$^7$, —C(O)N(OH)R$^6$, —C(O)NR$^5$R$^4$, —NR$^6$C(O)R$^4$, —CR$^6$(NH$_2$)CO$_2$R$^6$, —NHCX$^1$X$^2$CO$_2$R$^6$, —N(OH)C(O)NR$^6$R$^7$, —N(OH)C(O)R$^4$, —NHC(O)NR$^6$R$^7$, —C(O)NHNR$^6$R$^7$, —C(O)N(OR$^5$)R$^6$ with the proviso that any hetero atom substituent in $R^1$ must be separated from the exocyclic sulphur atom by at least two carbon atoms;
and where:
  $R^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, —OR$^6$, —NHCX$^1$X$^2$CO$_2$R$^6$ or —NR$^6$R$^7$;
  $R^5$ is hydrogen, alkyl, alkenyl, alkynyl, cycloalkyl, cycloalkenyl, aryl, arylalkyl heteroaryl, heteroarylalkyl, reduced heteroaryl or reduced heteroarylalkyl;
  $R^6$ and $R^7$ are independently hydrogen, alkyl, alkenyl, alkynyl, cycloalkyl, cycloalkenyl, aryl, arylalkyl, heteroaryl, reduced heteroaryl, reduced heteroarylalkyl or —(CH$_2$)$_n$(OR$^5$)$_m$ wherein n is 1 to 12, wherein m is 1 to 3; and X$^1$ and X$^2$ are independently hydrogen, alkyl, alkenyl, alkynyl, cycloalkyl, cycloalkenyl, aryl, heteroaryl, arylalkyl, heteroarylalkyl, reduced heteroaryl or reduced heteroarylalkyl.

18. The method of claim 17 wherein the disorder caused by obesity is selected from hyperlipaemia, hyperlipidaemia, hyperglycaemia (type II diabetes), hypertension, cardiovascular disease, stroke, gastrointestinal disease and gastrointestinal conditions.

19. A method for the prevention or treatment of obesity or a disorder caused by obesity, the method comprising administering to a patient a compound of formula (Ia) or (IIa) as defined in any one of claims 1 to 5 or a pharmaceutically acceptable salt, ester, amide, or pro-drug thereof.

20. The method of claim 17 wherein the compound of formula (I) inhibits an enzyme whose preferred mode of action is to catalyse the hydrolysis of an ester functionality.

21. The method of claim 17 wherein n is 2 to 10 and R$^5$ is C$_2$–C$_{10}$ alkyl, with the proviso that any hetero atom substituent in R$^1$ must be separated from the exocyclic sulphur atom by at least two saturated carbon atoms.

22. The method of claim 17, wherein the compound of formula (I) is a compound of formula (Ia):

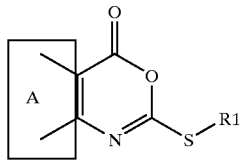

(Ia)

or a pharmaceutically acceptable salt, ester, amide or pro-drug thereof;
wherein in formula (Ia):

A is a 6-membered aromatic ring optionally substituted with or more groups as defined below for R$^1$; and R$^1$ is a branched C$_{4-50}$alkyl or unbranched C$_{3-25}$alkyl, a branched C$_{4-50}$alkylether or unbranched C$_{3-25}$alkylether, a branched C$_{4-50}$alkylpolyether or unbranched C$_{3-25}$alkylpolyether, C$_{2-25}$alkenyl, C$_{2-25}$alkynyl, C$_{3-10}$cycloalkyl, C$_{3-10}$cyclonalkenyl, aryl, arylC$_{2-25}$alkyl, reduced arylC$_{1-25}$alkyl, arylC$_{2-25}$alkenyl, heteroaryl, heteroarylC$_{2-25}$alkyl, heteroarylC$_{2-25}$alkenyl, reduced aryl, reduced heteroaryl, reduced heteroarylC$_{2-25}$alkyl or a substituted derivative of any of the foregoing groups, wherein the substituents are one or more independently of halogen, alkyl, halosubstituted alkyl, aryl, arylalkyl, heteroaryl, reduced heteroaryl, reduced heteroarylalkyl, arylalkoxy, cyano, nitro, —C(O)R$^4$, —CO$_2$R$^5$, —SOR$^4$, —SO$_2$R$^4$, —NR$^6$R$^7$, —OR$^6$, —SR$^6$, —C(O)CX$^1$X$^2$NR$^6$R$^7$, —C(O)N(OH)R$^6$, —C(O)NR$^5$R$^4$, —NR$^6$C(O)R$^4$, —CR$^6$(NH$_2$)CO$_2$R$^6$, —NHCX$^1$X$^2$CO$_2$R$^6$, —N(OH)C(O)NR$^6$R$^7$, —N(OH)C(O)R$^4$, —NHC(O)NR$^6$R$^7$, —C(O)NHNR$^6$R$^7$, —C(O)N(OR$^5$)R$^6$ with the proviso that any hetero atom substituent in R$^1$ must be separated from the exocyclic sulphur atom by at least two carbon atoms; and where:

R$^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, —OR$^6$, —NHCX$^1$X$^2$CO$_2$R$^6$ or —NR$^6$R$^7$;

R$^5$ is hydrogen, alkyl, alkenyl, alkynyl, cycloalkyl, cycloalkenyl, aryl, arylalkyl heteroaryl, heteroarylalkyl, reduced heteroaryl or reduced heteroarylalkyl;

R$^6$ and R$^7$ are independently hydrogen, alkyl, alkenyl, alkynyl, cycloalkyl, cycloalkenyl, aryl, arylalkyl, heteroaryl, reduced heteroaryl, reduced heteroarylalkyl or —(CH$_2$)$_n$(OR$^5$)$_m$ wherein n is 1 to 12, wherein m is 1 to 3; and X$^1$ and X$^2$ are independently hydrogen, alkyl, alkenyl, alkynyl, cycloalkyl, cycloalkenyl, aryl, heteroaryl, arylalkyl, heteroarylalkyl, reduced heteroaryl or reduced heteroarylalkyl with the proviso that when A is phenyl disubstituted at the 6 and 7 positions with methoxy groups, R$^1$ is not CH$_2$CH═CHPh.

23. The method of claim 22, wherein the compound of formula (Ia) is a compound of formula (IIa):

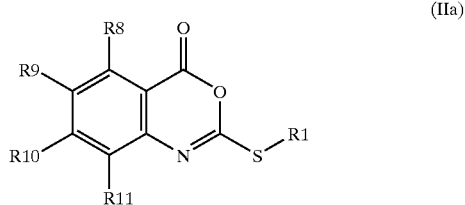

(IIa)

or a pharmaceutically acceptable salt, ester, amide or pro-drug thereof;
wherein:

R$^1$, R$^4$, R$^5$, R$^6$, R$^7$, X$^1$ and X$^2$ are as defined in claim 22 for formula (Ia); and R$^8$, R$^9$, R$^{10}$, R$^{11}$ are each independently hydrogen, halo, hydroxy, amino, nitro, cyano, or a group R$^1$, as defined in claim 22 for formula (Ia), or a group R$^{12}$Q where Q is O, CO, CONH, NHCO, S, SO, SO$_2$, or SO$_2$NH$_2$ and R$^{12}$ is hydrogen or a group R$^1$ as defined in claim 22 for formula (Ia) with the proviso that when R$^1$ is CH$_2$CH═CHPh, R$^8$ and R$^{11}$ are H and R$^9$ is OMe; R$^{10}$ is not OMe, or a group R$^1$R$^2$N where R$^1$ is as defined in claim 22 for formula (Ia) and R$^2$ hydrogen or R$^1$, with the proviso that any hetero atom substituent in R$^1$ and/or must be separated from the nitrogen atom substituent by at least two carbon atoms.

24. The method of claim 23, wherein the compound of formula (IIa) R$^1$ is an unbranched alkyl group having from 3 to 25 carbon atoms; an aryl up; an arylalkyl group wherein the alkyl moiety has from 2 to 25 carbon atoms; or an arylaryl group, wherein the arylalkyl group or the arylaryl group may be separated by a spacer, and where the spacer can be one or more of an ester, amide, O, CH$_2$ or a ketone;

R$^8$ is hydrogen or fluorine;

R$^9$ is lower branched or unbranched alkyl having 1 to 10 carbon atoms; cyclic alkyl having 3 to 10 carbon atoms; haloalkyl or a halogen;

R$^{10}$ is hydrogen lower branched or unbranched alkyl having 1 to 10 carbon atoms; cyclic alkyl having 3 to 10 carbon atoms; haloalkyl; or halogen; and R$^{11}$ is hydrogen lower branched or unbranched alkyl having 1 to 10 carbon atoms or a halogen.

25. The method of claim 23 or 24, wherein in the compound of formula (IIa) R$^1$ is an unbranched alkyl with 8, 9, 10, 11, 12, 13, 14, 15, 16, 17, 18, 19 or 20 carbon atoms;

a phenyl group; a phenylalkyl group wherein the alkyl is an unbranched group containing from 2 to 20 carbon atoms; or a phenoxyphenyl group, wherein the phenyl group is optionally substituted with methyl, halide or halomethyl where the halide is F, Cl, Br or I, $R^8$ is hydrogen, and $R^9$, $R^{10}$ and $R^{11}$ are independently H or methyl.

26. The method of claim 23 wherein the compound of formula (IIa) is selected from the group consisting of:

6-Methyl-2-octylthio-4H-3,1-benzoxazin-4-one;

7-Methyl-2-octylthio-4H-3,1-benzoxazin-4-one;

8-Methyl-2-octylthio-4H-3,1-benzoxazin-4-one;

6-Methyl-2-phenylthio-4H-3,1-benzoxazin-4-one;

6-Methyl-2-(10-phenyldecyl)thio-4H-3,1-benzoxazin-4-one;

6-Methyl-2-icosylthio-4H-3,1-benzoxazin-4-one;

6-Methyl-2-hexadecylthio-4H-3,1-benzoxazin-4-one;

pharmaceutically acceptable salts thereof, esters thereof, amides thereof and prodrugs thereof.

27. The method of claim 20 wherein the enzyme is esterase, a phosphoesterase or a lipase enzyme.

28. The method of claim 17 wherein in the step of administering the compound, the compound is administered in an amount sufficient to reduce levels of toxins that are stored in body fat.

29. The method of claim 17 wherein the step of administering the compound to a patient comprises administering the compound to humans.

30. The method of claim 17 wherein the step of administering the compound to a patient comprises administering the compound to animals.

* * * * *